(12) United States Patent
Guala

(10) Patent No.: US 7,666,170 B2
(45) Date of Patent: Feb. 23, 2010

(54) MEDICAL VALVE CONNECTOR

(75) Inventor: Gianni Guala, Turin (IT)

(73) Assignee: Industrie Borla S.p.A., Moncaleri (Torino) (IT)

( * ) Notice: Subject to any disclaimer, the term of this patent is extended or adjusted under 35 U.S.C. 154(b) by 324 days.

(21) Appl. No.: 11/492,747

(22) Filed: Jul. 25, 2006

(65) Prior Publication Data
US 2007/0043334 A1   Feb. 22, 2007

(30) Foreign Application Priority Data
Jul. 25, 2005   (IT)   ................ TO2005A0515

(51) Int. Cl.
*A61M 5/00* (2006.01)
(52) U.S. Cl. .............. 604/249; 604/246; 604/533; 604/534; 604/535; 604/537
(58) Field of Classification Search ............. 604/247, 604/249, 256, 246, 248, 533–539
See application file for complete search history.

(56) References Cited

U.S. PATENT DOCUMENTS

| | | | |
|---|---|---|---|
| 4,387,879 A * | 6/1983 | Tauschinski | ............. 251/149.1 |
| 6,089,541 A | 7/2000 | Weinheimer et al. | |
| 6,206,861 B1 | 3/2001 | Mayer | |
| 6,299,132 B1 | 10/2001 | Weinheimer et al. | |
| 6,543,745 B1 | 4/2003 | Enerson | |
| 7,306,566 B2 * | 12/2007 | Raybuck | .............. 600/576 |
| 7,470,254 B2 * | 12/2008 | Basta et al. | ........... 604/167.04 |
| 2005/0090805 A1 | 4/2005 | Shaw et al. | |

OTHER PUBLICATIONS

European Search Report, Application No. EP 06 11 7298, Nov. 13, 2006.

* cited by examiner

*Primary Examiner*—Kevin C Sirmons
*Assistant Examiner*—Laura C Schell
(74) *Attorney, Agent, or Firm*—Heslin Rothenberg Farley & Mesiti P.C.; Victor A. Cardona, Esq.

(57) ABSTRACT

A medical valve connector comprising a tubular body having an inlet fitting of the male luer or luer-lock type with an inner tubular element displaceable axially from a retracted position for closing a passage of flow towards an outlet fitting to an advanced position for opening said passage of flow. A tubular body made of elastic material, set between the inlet and outlet fittings, tends to keep the inner tubular element in the retracted position. Also the outlet fitting can rotate and axially translate between a retracted position and an advanced position.

18 Claims, 19 Drawing Sheets

MEDICAL VALVE CONNECTOR

CROSS REFERENCE TO RELATED APPLICATIONS

This application is a claims priority from Italian Patent Application No. TO2005A000515 filed on Jul. 25, 2005, the entire disclosure of which is incorporated herein by reference.

FIELD OF THE INVENTION

The present invention relates in general to connectors, for example medical ones, which comprise a tubular body having an inlet fitting of the male luer or luer-lock type which can be connected by screwing to a complementary female luer or luer-lock fitting, an outlet fitting coaxial to the inlet fitting, and means defining a passage of flow between said inlet and outlet fittings.

More in particular, the invention relates to a medical connector of the type defined above with valve function, i.e., in which the passage of flow between the inlet and outlet fittings is kept closed substantially hermetic way in the absence of the complementary female luer or luer-lock fitting screwed on the male inlet luer or luer-lock fitting.

STATE OF THE PRIOR ART

From the documents Nos. U.S. Pat. No. 6,299,132 and U.S. Pat. No. 6,543,745 a valve connector of this sort is known, in which the male luer-lock inlet fitting comprises an outer tubular element and an inner tubular element axially displaceable but not rotationally displaceable with respect to the tubular outer body, following upon coupling with the complementary female luer-lock fitting, from a retracted position for closing to an advanced position for opening of the passage of flow. In said known solutions, sealing means are provided that can slide between the inner tubular element of the male luer-lock inlet fitting and the body of the connector, constituted by annular gaskets housed in corresponding external grooves of the inner tubular element. Elastic means are moreover provided, which tend to keep the inner tubular element of the male luer-lock inlet fitting in the aforesaid retracted position, constituted in the first case by a spring or else by an elastic body, and in the second case also by a spring. The passage of flow in the advanced opening position of the inner tubular body is in both cases defined by a generally annular peripheral path, in which the flow is in contact with the wall of the tubular body of the connector.

In addition to a relatively complex construction, on account of the conformation both of the sliding-seal means through the inner tubular element of the male luer-lock fitting, and of the passage of flow, these known solutions entail the risk of contamination of the flow itself from the inlet fitting to the outlet fitting of the connector.

SUMMARY OF THE INVENTION

The purpose of the present invention is to overcome the aforesaid drawbacks and, in particular, to provide a medical valve connector of the type defined at the start of the present description, which is built in a simpler and more essential way and is moreover designed to eliminate the risks of contamination of the flow that traverses it.

According to the invention, the above purpose is achieved basically thanks to the fact that said means that define the passage of flow, said sliding-seal means, and said elastic means are integrated in a generally tubular body made of elastic material set axially in a sealed way between said inlet and outlet fittings of the valve connector.

According to a first embodiment of the invention, the inner tubular element of the male luer or luer-lock inlet fitting is open at its internal end, and the tubular body made of elastic material is formed with a transverse diaphragm having a pre-cut, which can be opened elastically by said internal end of said inner tubular element when the latter sets itself in the advanced opening position.

According to a variant of the invention, the inner tubular element of the male luer or luer-lock inlet fitting is closed at its internal end and has in the proximity thereof at least one radial passage, and the tubular body of elastic material defines a chamber which is open towards the outlet fitting and within which said at least one radial passage sets itself in the advanced position for opening the aforesaid inner tubular element.

The outlet fitting of the valve connector according to the invention can consist of a simple tubular element for direct connection to a pipe, or else of a fitting of the female luer or luer-lock type that can be engaged by screwing to a complementary male luer or luer-lock fitting. In either case, the outlet fitting can be advantageously connected to the body of the connector in a rotary way. In the case of an outlet fitting of the female luer or luer-lock type, this can be conveniently axially translatable from a retracted position to an advanced position against the action of the aforesaid tubular body of elastic material, and provided between said outlet fitting and the body of the connector are first and second one-directional detent means, of which the first prevent rotation between the outlet fitting and the body of the connector in a first direction of rotation corresponding to the direction of screwing of the complementary male luer or luer-lock fitting to said outlet fitting when the latter is set in the aforesaid retracted position, and the second prevent rotation between said outlet fitting and the body of the connector in a second direction of rotation corresponding to the direction of unscrewing of the complementary male luer-lock fitting when the outlet fitting is translated into the advanced position. In this way, screwing between the female luer or luer-lock fitting of the connector and the complementary male luer or luer-lock fitting is obtained normally as in the case of traditional medical connectors of the same type, whilst unscrewing thereof can be performed only following upon a translation of the female luer or luer-lock fitting towards the inside of the body, performed positively against the action of the tubular body made of the elastic material. In the absence of said positive and voluntary translation, a rotation of unscrewing of the complementary male luer or luer-lock fitting simply causes a corresponding rotation of the female luer or luer-lock fitting of the connector with respect to the body. This advantageously prevents any accidental or undesirable separation between the connector according to the invention and the medical line connected in use to the complementary male luer or luer-lock fitting.

When the male luer or luer-lock inlet fitting of the connector is in turn engaged with a complementary female luer or luer-lock fitting, and consequently its inner tubular element is set in the advanced opening position, the translation of the female luer or luer-lock outlet fitting of the connector towards the advanced position is blocked and prevented by the contrast against said inner tubular element. In this condition therefore, unscrewing of the complementary male luer or luer-lock fitting is prevented on account of the free rotation of the female luer or luer-lock outlet fitting with respect to the body of the connector, in the direction of rotation which corresponds to unscrewing of the complementary male luer or luer-lock fitting.

According to a further characteristic of the invention, the inner tubular element of the male luer or luer-lock inlet fitting of the connector can moreover be conveniently provided with manoeuvring means projecting on the outside of the body of the connector for controlling manually axial displacement of the inner tubular element from the retracted position to the advanced one, even in the absence of coupling with the complementary female luer or luer-lock fitting, so as to be able to provide, if need be, manual engagement of the connector precisely through a controlled opening of the passage of flow between the inlet fitting and the outlet fitting.

BRIEF DESCRIPTION OF THE DRAWINGS

Further characteristics of the invention will emerge clearly evident in the course of the ensuing detailed description, with reference to the annexed plate of drawings, which are provided purely by way of non-limiting example and in which.

DETAILED DESCRIPTION OF THE INVENTION

Figure 1:
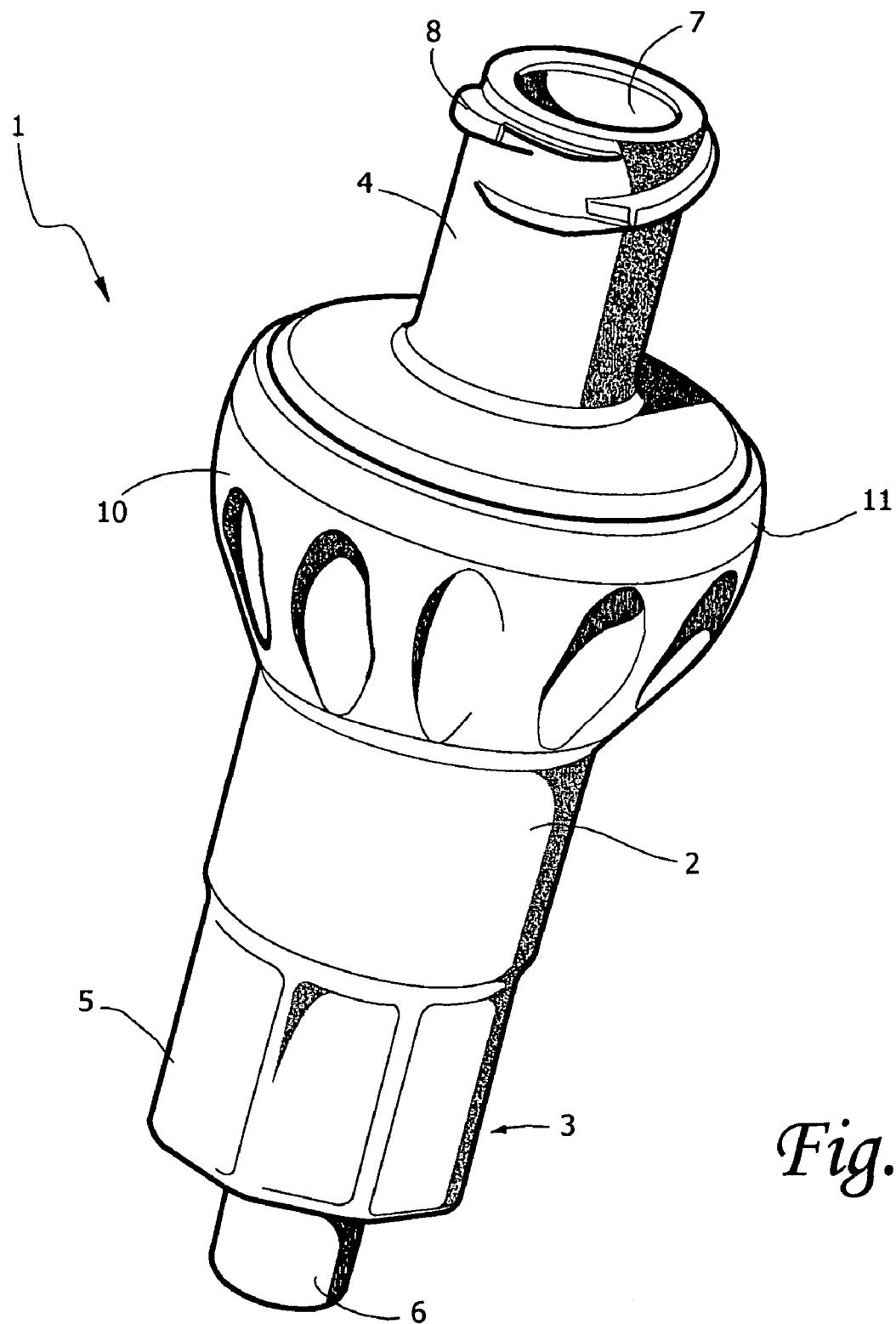
FIG. 1 is a schematic perspective view of a first example of embodiment of the medical valve connector according to the invention.
Figure 2:
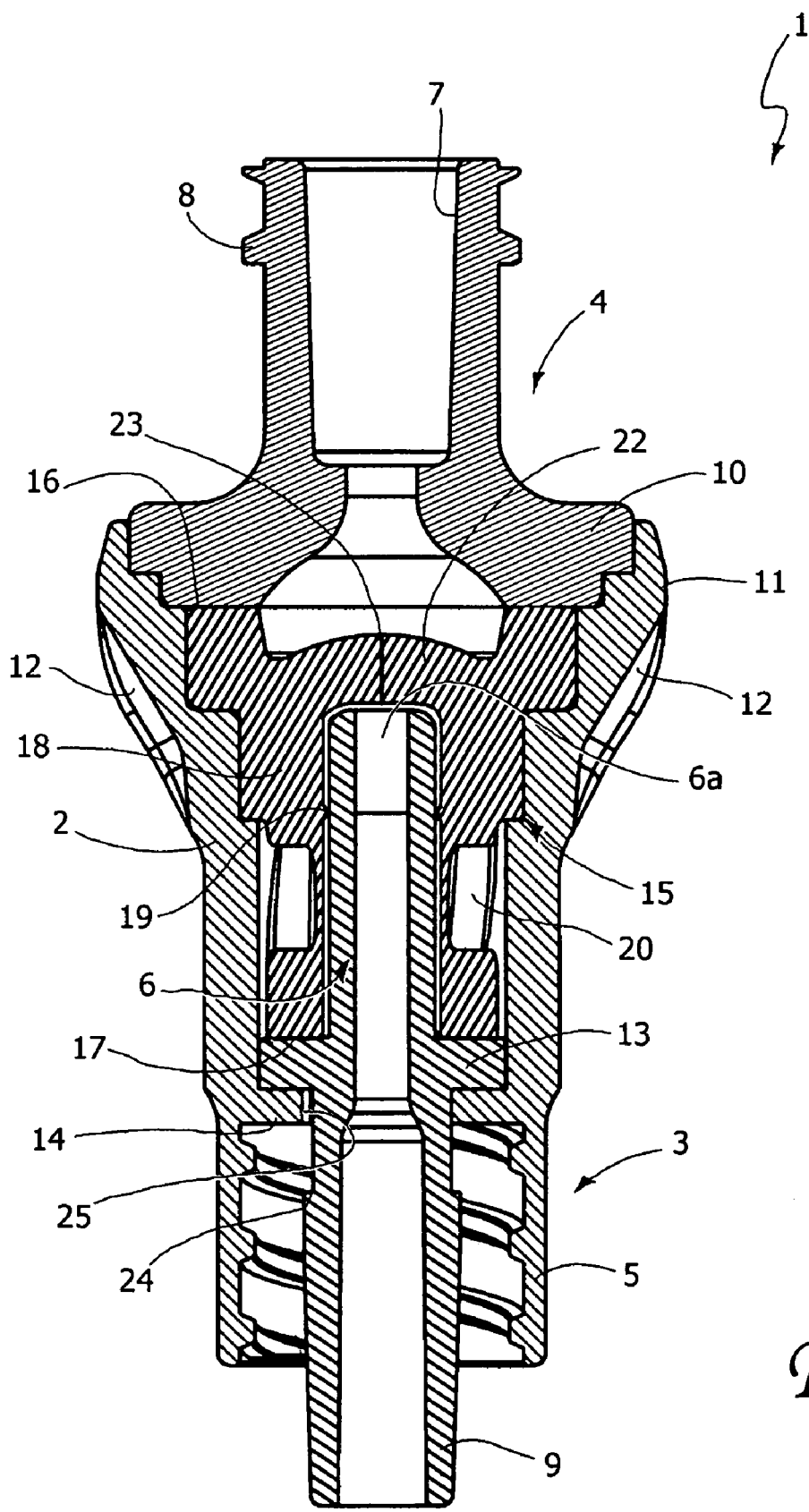
FIG. 2 is an axial cross-sectional view of the connector in a first operating condition.
Figure 3:
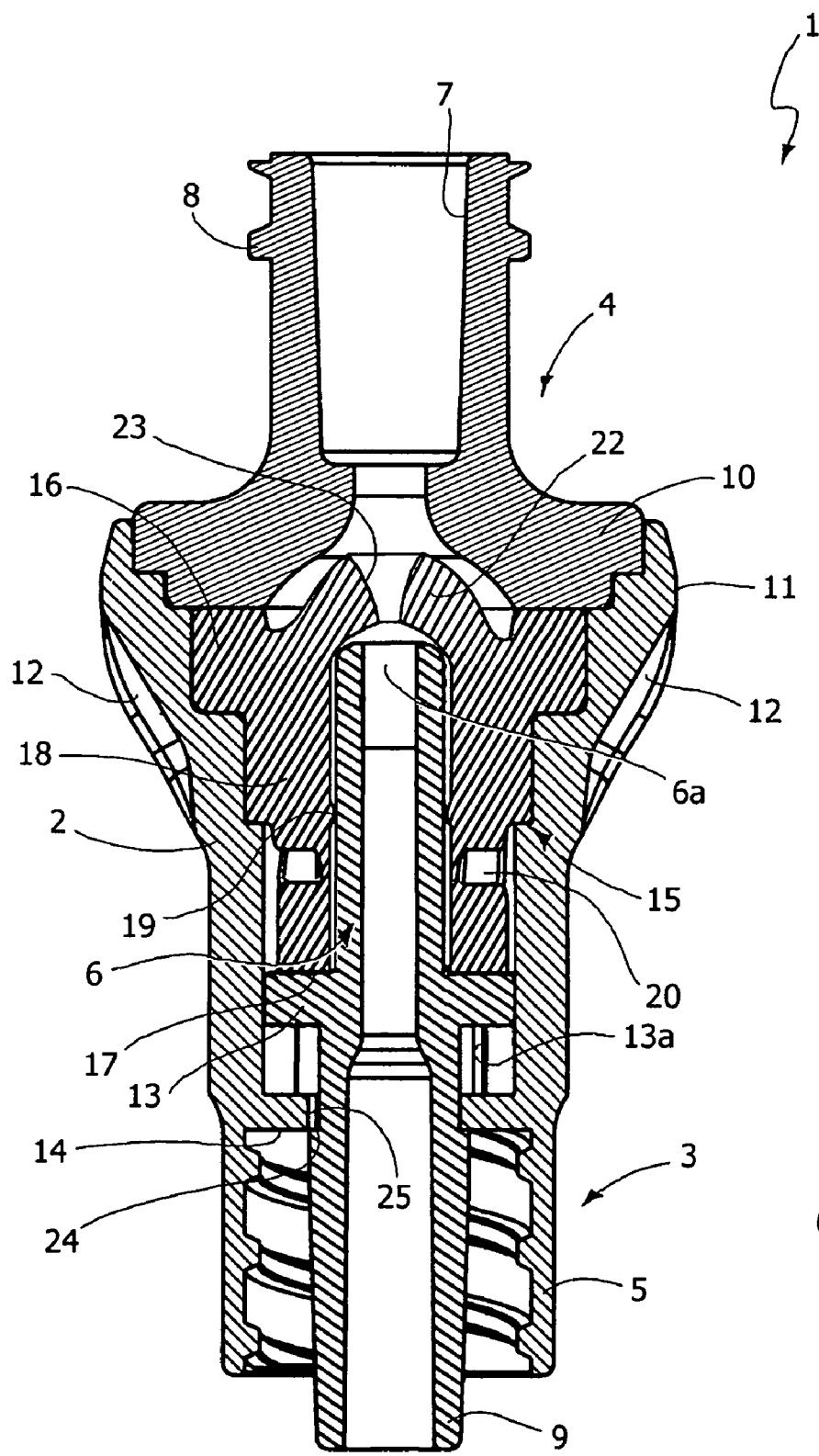
FIG. 3 is a view similar to that of FIG. 2 in a second operating condition of the connector.

With initial reference to FIGS. 1 to 3, number 1 designates as a whole a valve connector according to the invention, basically comprising a tubular body 2 provided, coaxially with respect to its opposite ends, with an inlet fitting 3 and with an outlet fitting 4, both of which can be connected, in the way clarified in what follows, to respective parts of a medical line, for example an infusion line. The components of the medical connector 1 described above are all made of moulded plastic material.

With reference now in greater detail to FIG. 2, the inlet fitting 3 is of the male luer or luer-lock type, with an external hollow element 5 internally threaded and formed integrally with the body 2, and an inner tubular element 6, which can slide axially with respect to the external element 5. Said male luer-lock fitting 3 (referred to in what follows for reasons of brevity as "inlet fitting") can be connected by screwing, in a way in itself known, to a complementary female luer or luer-lock fitting, for example generally similar to the outlet fitting 4. Said female luer-lock fitting 4 (in what follows simply referred to as "outlet fitting") has a cavity having a conical surface 7 and an external thread 8. When a female luer-lock connector of this sort is engaged with the inlet connector 3, by screwing the thread 8 within the internal thread of the external element 5, the cavity having a conical surface 7 engages the external surface of the inner tubular element 6, designated by 9, which is also conical, with a conicity complementary to that of the cavity 7.

In the case of the example described herein, the outlet fitting 4 has an annular flange 10 rigidly fixed within a widened end part 11 of the body 2, which has an ergonomic conformation with recesses 12 designed to facilitate manual gripping thereof.

As mentioned previously, the inner tubular element 6 of the inlet fitting 3 is axially mobile with respect to the body 2 between the retracted position, represented in FIG. 2, and an advanced position in the direction of the outlet fitting 4, represented in FIG. 3. Said inner tubular element 6 is formed, approximately in a median area thereof, with an annular flange 13 of polygonal shape or star shape, coupled in a slidable but not rotary way with corresponding internal longitudinal grooves 13a of the body 2. The flange 13, in the retracted position of FIG. 2, rests against an internal annular arrest collar 14, formed integrally with the body 2. This position is maintained thanks to the action of a tubular body of elastic material 15, which, according to the invention, is set substantially in a sealed way between the inlet fitting 3 and the outlet fitting 4.

This body of elastic material 15 integrates, according to the invention, three substantial functions: a first function, as mentioned, of thrust of the inner tubular element 9 towards the retracted position; a second function of sliding seal between the inner tubular element 6 and the body 2; and a third function consisting in the definition of a passage of flow between the inlet fitting 3 and the outlet fitting 4.

Figure 12:
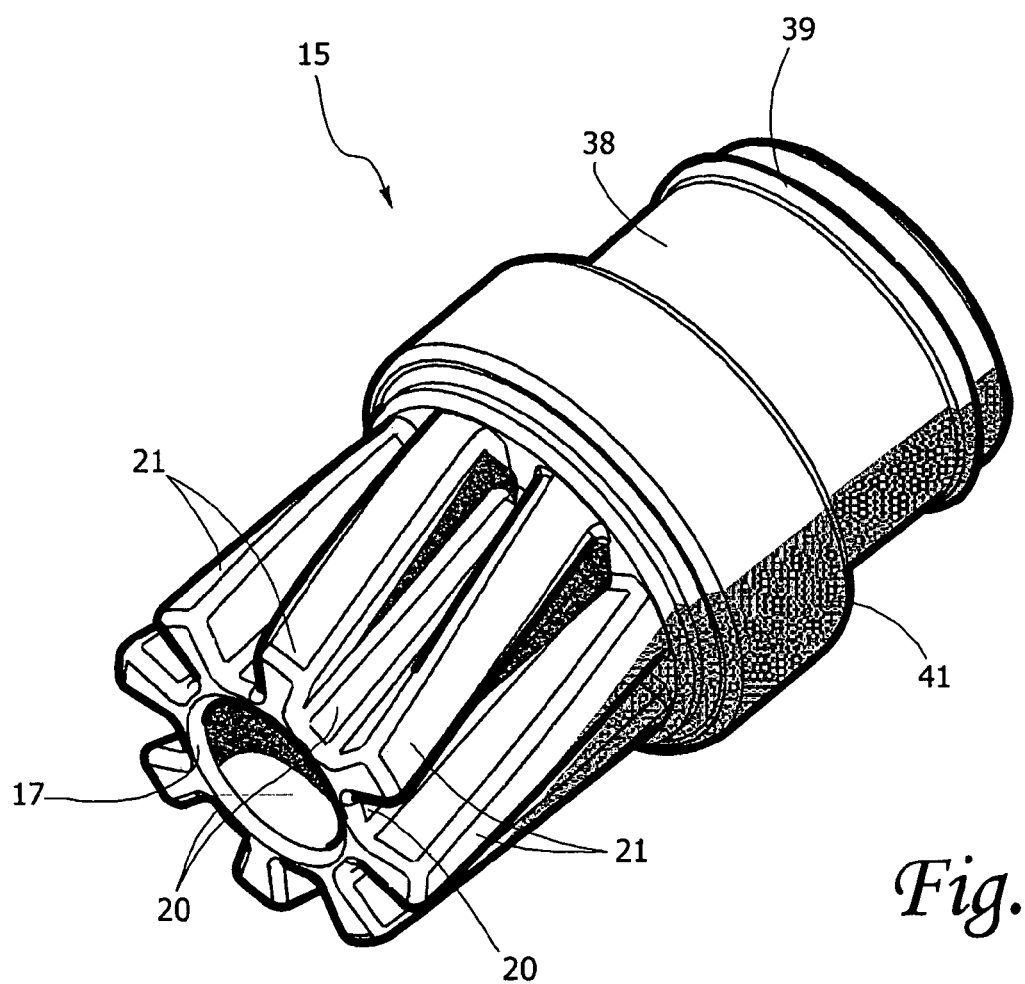
FIG. 12 is a perspective view, at a larger scale, of the elastic tubular body of the connector according to FIGS. 6 to 9.
Figure 13:
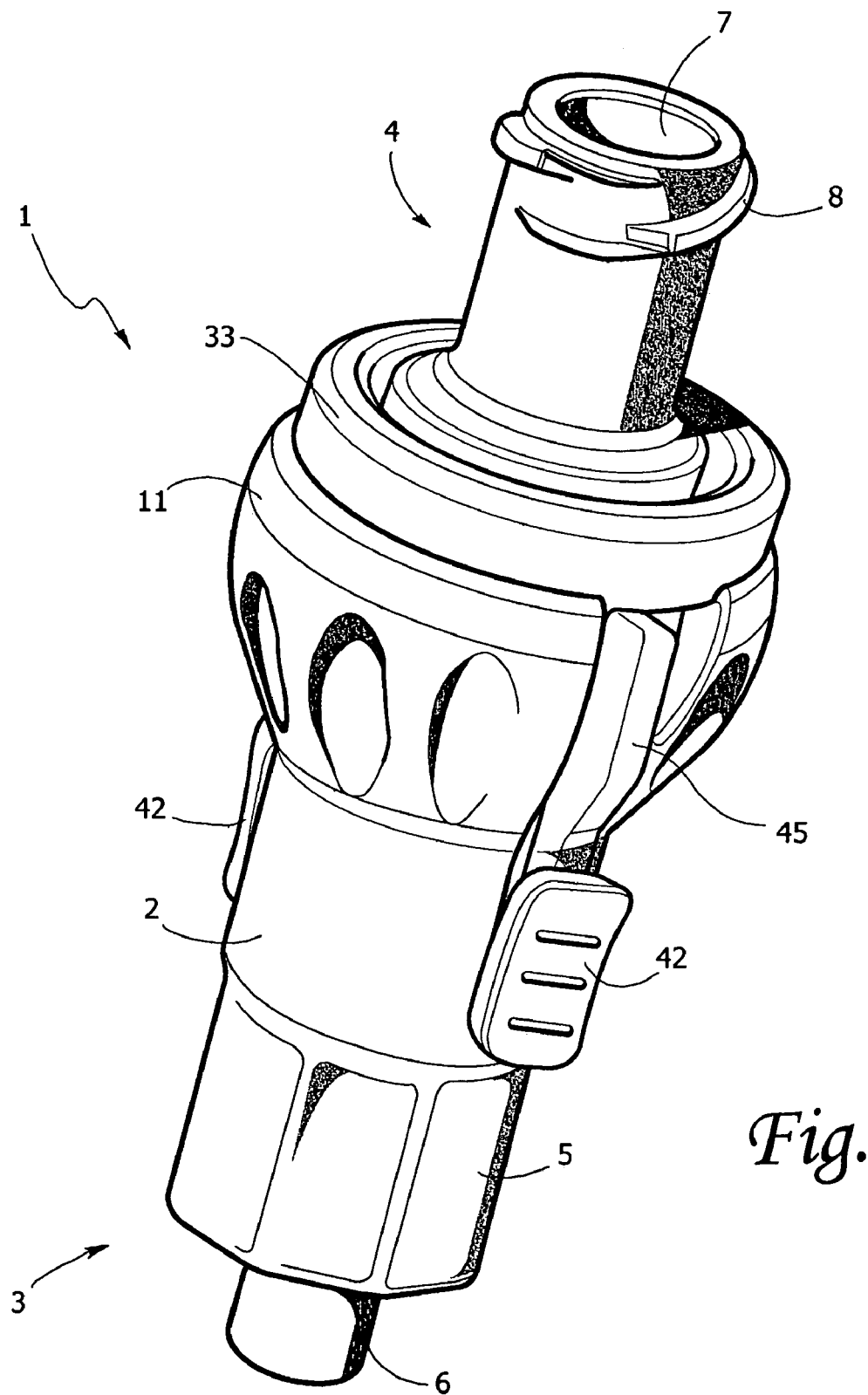
FIG. 13 is a view similar to that of FIG. 1 showing a fourth variant of the connector according to the invention.
Figure 14:
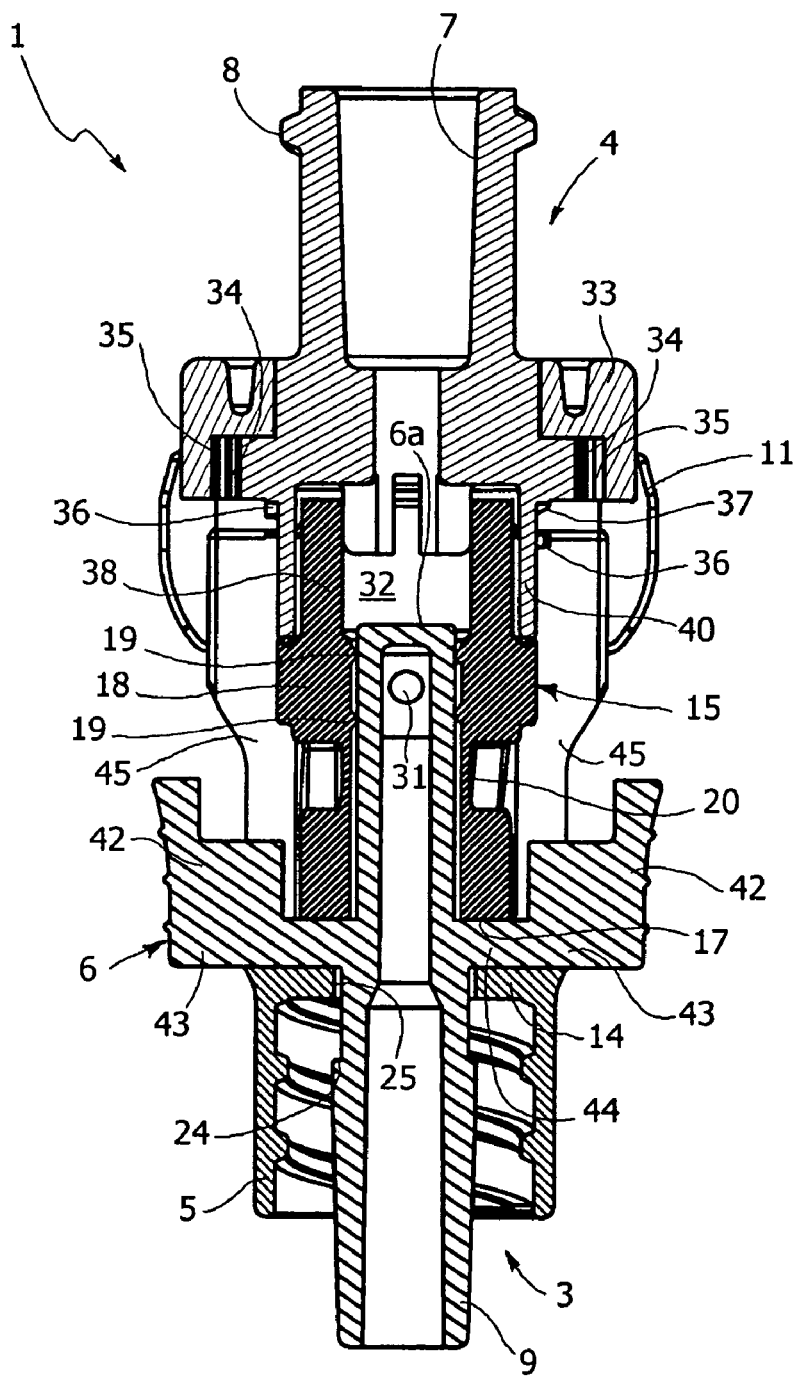
FIG. 14 is an axial sectional view of the connector of FIG. 13 in a first operating condition.

In the embodiment described here, the tubular body of elastic material 15 has, at one end, an annular part 16 in front-sealing contact against the flange 10 of the outlet fitting 4 and in lateral-sealing contact with the internal wall of the body 2, an opposite end 17 resting against the annular flange 13 of the inner tubular element 6, and an intermediate part 18, formed internally with one or more integral seal rings 19 in sliding contact against the wall of the inner tubular element 6 and formed externally with a wall 20 that is elastically more compliant in an axial direction. Said wall 20 conveniently has a conformation with alternating helical ribbings and grooves 20, 21, in the way represented in FIG. 12, albeit with reference to an elastic tubular body 15 of a shape different from that of FIGS. 2 and 3, which will now be further described in greater detail in what follows.

In addition, the elastic tubular body 15 of the embodiment described here has, between the end 16 and the intermediate part 18, a transverse diaphragm 22 formed with a central pre-cut 23, which is normally closed hermetically as a result of an appropriate radial pre-loading between the elastic tubular body 15 and the body 2 of the connector 1.

The inner tubular element 6 has an internal end 6a facing the side of the diaphragm 22, open axially.

Operation of the connector set forth above is described in what follows.

In the absence of coupling between a female luer-lock fitting (as mentioned, generally corresponding to the outlet fitting 4) and the inlet fitting 3, the inner tubular element 6 of said inlet fitting 3 is kept by the elastic tubular body 15 in the retracted position represented in FIG. 2. In said condition, the passage of flow between the inlet fitting 3 and the outlet fitting 4 is obstructed, and hence closed hermetically, by the transverse diaphragm 22 of the elastic tubular body 15.

When a complementary female luer-lock fitting is engaged and screwed to the inlet fitting 3, the interaction between the corresponding conical surfaces causes axial translation of the inner tubular element 6 from the retracted position of FIG. 2 to the advanced position of FIG. 3. As a result of said advance, the inner tubular element 6 is pressed against the diaphragm 22 of the elastic tubular body 15 and opens the pre-cut 23, without, however, traversing the diaphragm 22 with its open end 6a, deforming accordingly the elastic tubular body 15 and thus opening the passage of flow between the inlet fitting 3 and the outlet fitting 4. During this movement, the inner tubular element 6 slides in a sealed way against the integral ring or rings 19 of the elastic body 15, and at the end of its travel (corresponding to the screwing home of the female luer-lock fitting engaged with the inlet fitting 3) the inner tubular element 6 is stopped in the advanced position, as a result of the contrast between external projections 24, formed at the end of the conical surface 9 and corresponding complementary projections 25 of the internal annular flange 14. Obviously, the conformation and arrangement of this system of arrest could differ from the one illustrated.

When the female luer-lock fitting thus screwed is unscrewed and decoupled from the inner tubular element 6, this is brought back by the elastic return of the tubular body 15 into the retracted position of FIG. 2, thus enabling reclosing of the pre-cut 23 and hence of the passage of flow between the inlet fitting 3 and the outlet fitting 4.

The variants of the connector that will be described hereinafter are generally similar to the embodiment illustrated previously, and only the differences will be described in detail, using the same reference numbers for the parts that are identical or similar.

Figure 4:
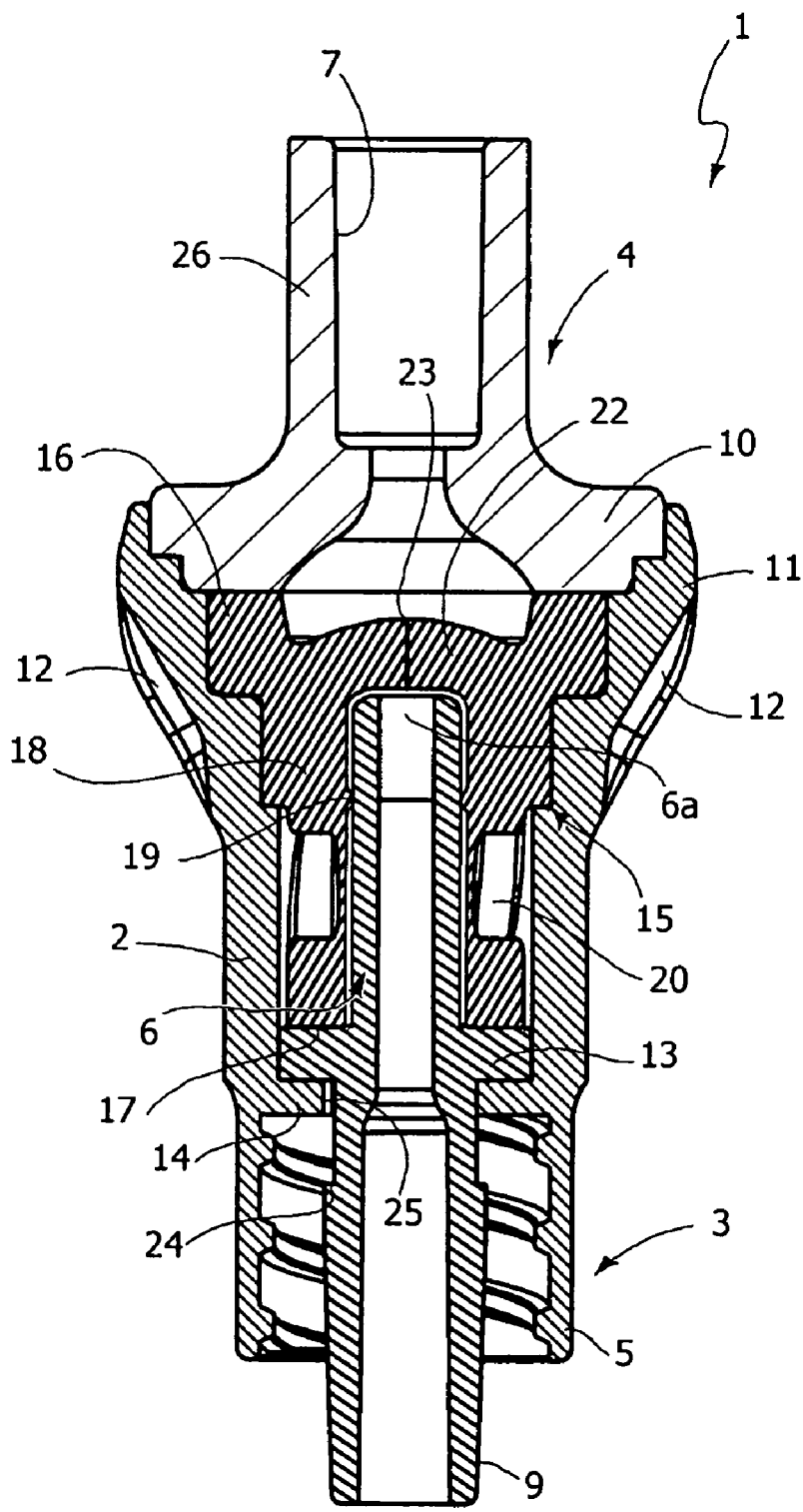
FIG. 4 is a view similar to that of FIG. 2 of a first variant of the connector.

In the case of FIG. 4, the connector differs from that of FIGS. 1 to 3 only as regards the fact that the outlet fitting 4 is constituted, instead of by a female luer-lock fitting, by a simple cylindrical tubular element 26 for direct connection to a pipe. In this case, the fitting 26 can be fixed rigidly to the widened part 11 of the body 2 of the connector 1, or else it can rotate freely in two directions.

Figure 5:
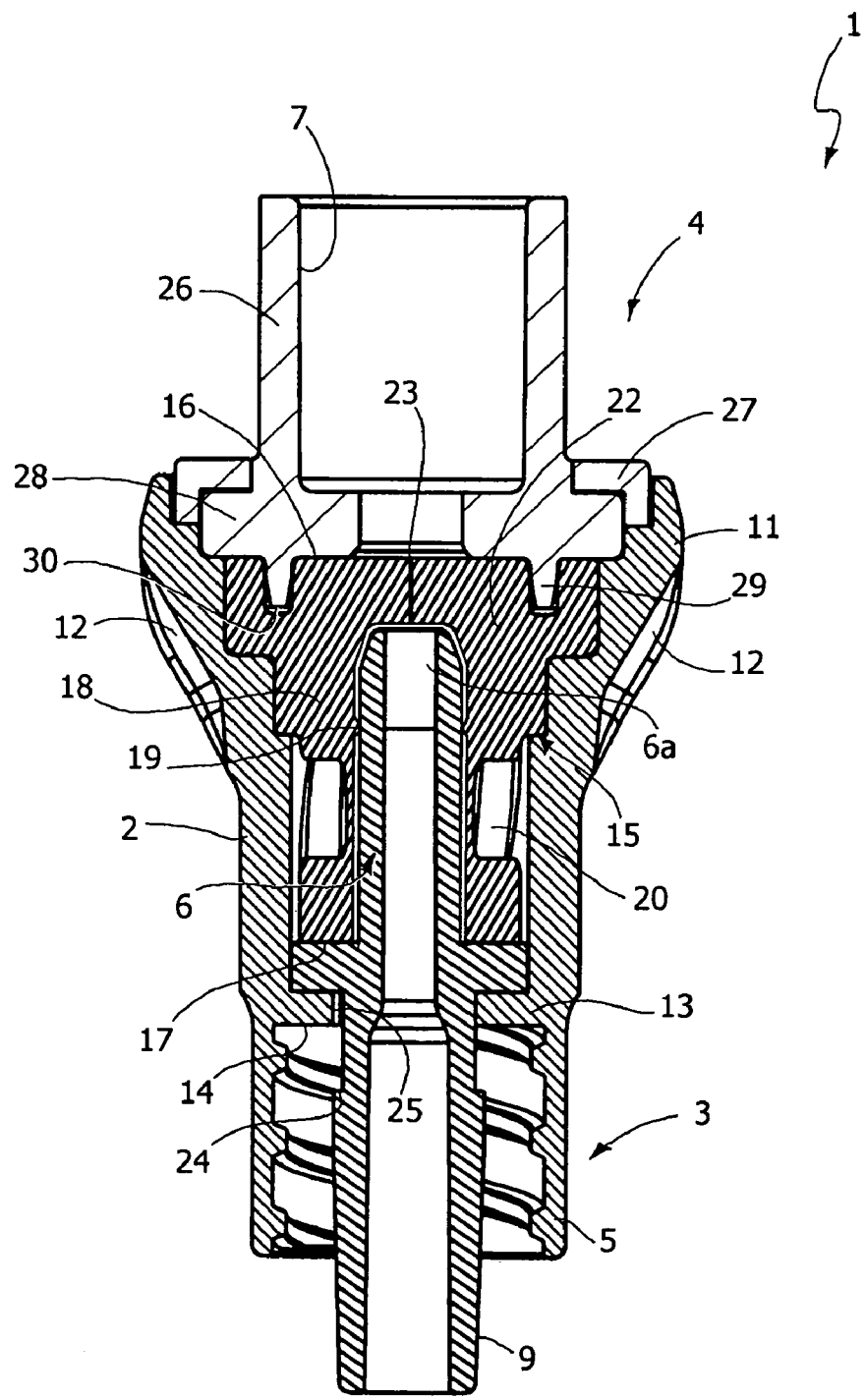
FIG. 5 is a view similar to that of FIG. 2 of a second variant of the connector.
Figure 6:
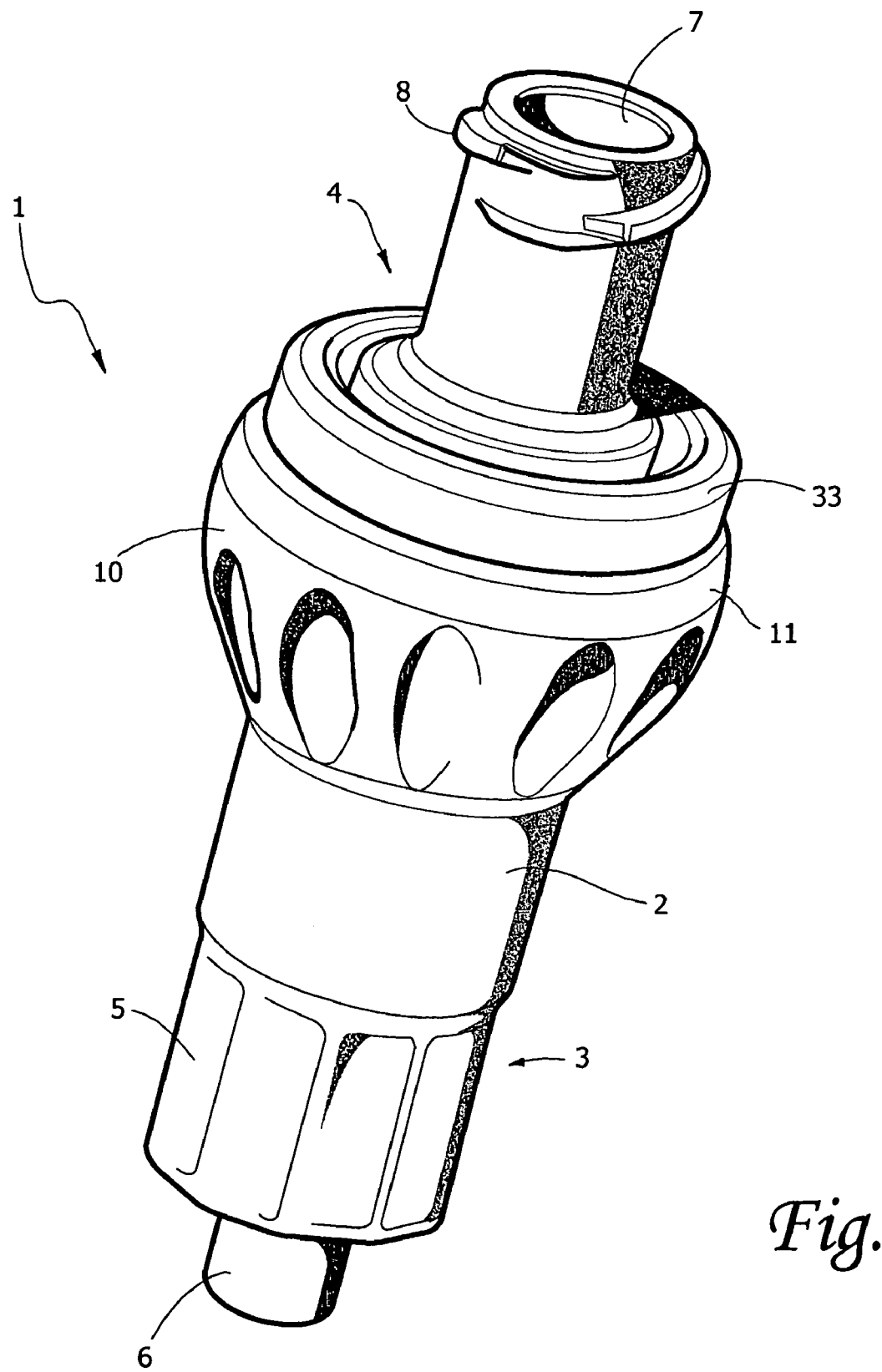
FIG. 6 is a perspective view similar to that of FIG. 1 of a third variant of the connector according to the invention.

In the embodiment represented in FIG. 5, the fitting 26, which is generally similar to that of FIG. 4, is connected to the body 2 in a rotary way, via a collar 27 fixed to the widened part 11 to withhold axially, but as mentioned in a rotary way, an annular flange 28 of the fitting 26 with respect to the body 2. Said flange 28 has an axial shank 29, engaged rotationally in a sealed way within a corresponding annular recess 30, formed at the end 16 of the tubular body of elastic material 15.

The variant represented in FIGS. 6 to 12 differs from the embodiment described with reference to FIGS. 1 to 3, in the first place, for the fact that the end 6a of the inner tubular element 6 of the inlet fitting 3 is closed, and in the proximity of said closed end 6a the inner tubular element 6 has one or more through radial holes 31. Furthermore, in this case the tubular body of elastic material 15 is without the diaphragm 22 with the pre-cut 23 of the previous embodiments.

The operation of opening/closing of the connector 1 according to this variant embodiment is similar to what has also been described previously. In the retracted position of the outer tubular element 6 of the inlet fitting 3, represented in FIG. 7 and corresponding to the absence of a complementary female luer-lock fitting engaged with the inlet fitting 3, the passage of flow through the fittings 3 and 4 is closed on account of the fact that the radial opening or openings 31 are obstructed by the portion 18 of the elastic tubular body 15, on opposite sides with respect to a pair of integral seal rings 19 thereof.

Figure 8:
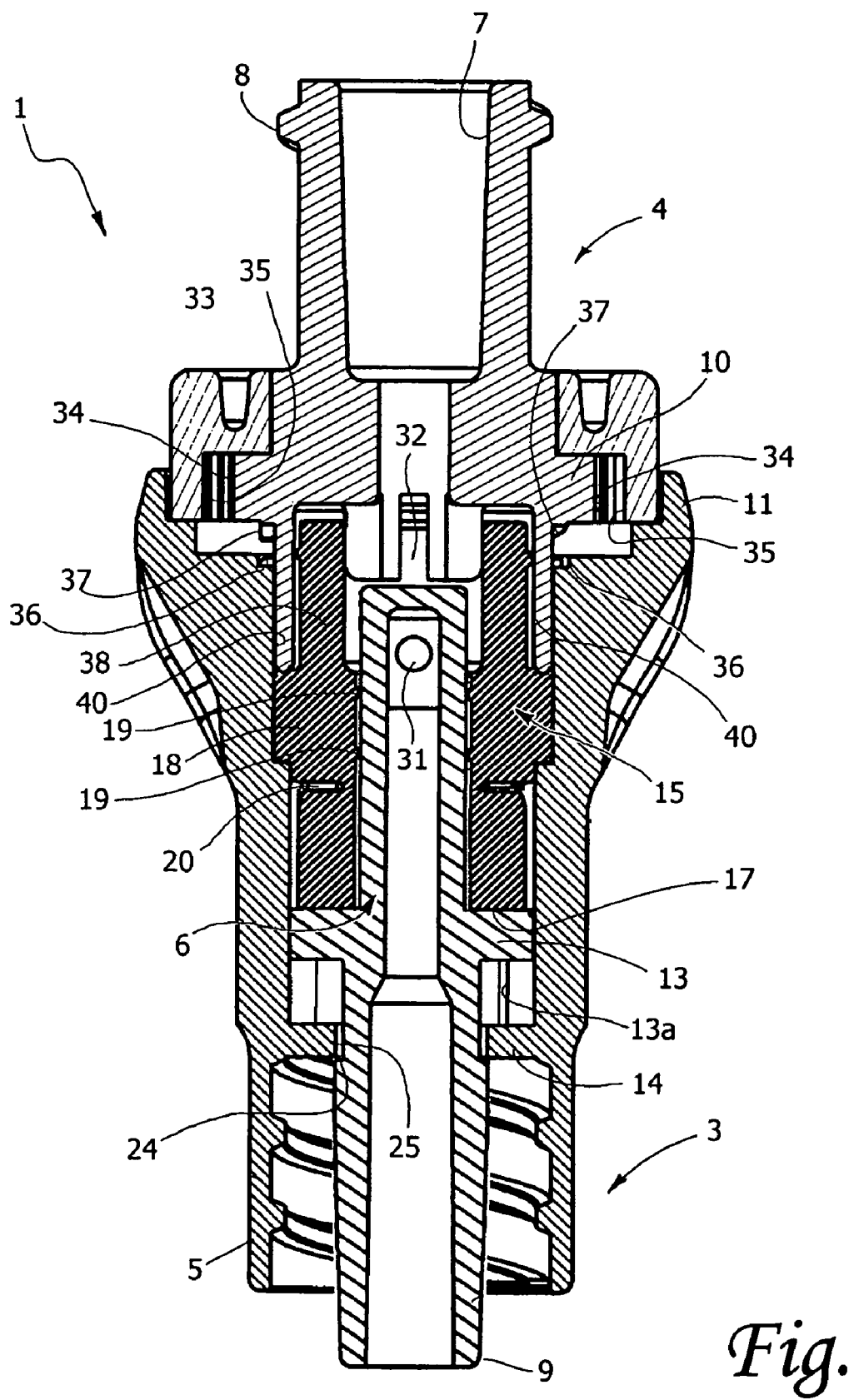
FIG. 8 is a view similar to that of FIG. 7, with the connector in a second operating condition.

Following upon advance of the inner tubular element 6, as a result of engagement of a complementary female luer-lock fitting within the inlet fitting 3, the side hole or holes 31 are freed from the elastic tubular body 15, in the way represented in FIG. 8, thus opening the passage of flow between the inlet and outlet fittings 3, 4 through a chamber 32 defined within the end 16 of the elastic tubular body 15.

When the complementary female luer-lock fitting is unscrewed and separated from the inlet fitting 3, the elastic tubular body 15 brings the inner tubular element 6 back into the retracted position of FIG. 7, interrupting again the passage of flow through the connector 1.

The second important difference between the variant of FIGS. 6 to 12 and the previous embodiments lies in the fact that the outlet fitting 4, also in this case constituted by a female luer-lock fitting, is connected to the body 2 of the connector 1 in both a rotationally and axially translatable way. For this purpose, the radial flange 10 is set between the widened part 11 of the body 2 and a collar 33 rigidly connected to said widened part 11, for example by means of welding or other systems. The flange 10 is in this case formed integrally with a ring of pawl-like sprung teeth 34, more clearly visible in FIG. 11, designed to co-operate in the way clarified in what follows with a ring of saw teeth 35, formed integrally within the collar 33 in the way represented in detail in FIG. 10. As will be seen in what follows, the pawls 34 and the teeth 35 define a first one-directional detent assembly via which the luer-lock fitting 4 cannot rotate with respect to the body 2 of the connector 1 in a first direction of rotation corresponding to screwing on said female luer-lock fitting 4 of a complementary male luer-lock fitting. This complementary male luer-lock fitting is not illustrated, in so far as it is conventional and generally corresponds to the inlet fitting 3, except for the fact that the corresponding external and internal tubular elements are normally made of a single piece.

Figure 11:
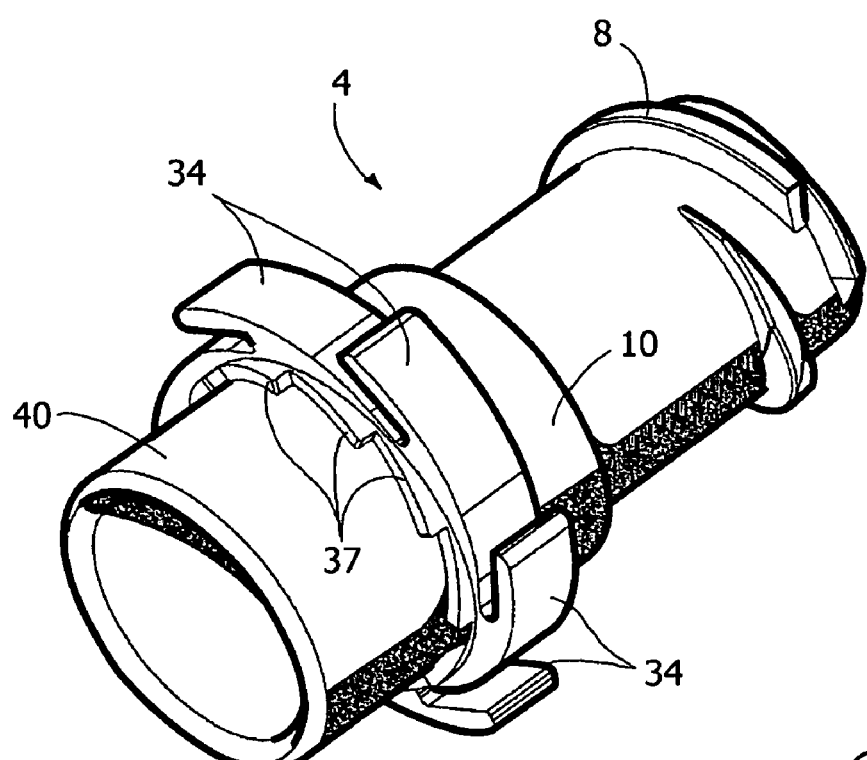
FIG. 11 is a perspective view, at a larger scale, of the outlet fitting of the connector represented in FIGS. 6 to 9.

With reference once again to FIG. 10, the widened part 11 of the body 2 is in turn formed internally with a ring of detent teeth 36, set opposed and staggered axially with respect to the saw teeth 35 of the collar 33, with which there is designed to co-operate in the way clarified in what follows a ring of saw teeth 37, which are also formed integrally with the outlet fitting 4 underneath the sprung pawls 34, in the way more clearly visible in FIG. 11. The teeth 36 and 37 define a second one-directional detent assembly designed to enable rotation of the fitting 4 with respect to the body 2 only in a second direction of rotation, opposite to the first, to enable, as will be seen, unscrewing of the complementary male luer-lock fitting screwed on the outlet fitting 4.

The flange 10 of the fitting 4, with the sprung pawls 34 and the saw teeth 37, is housed with axial play between the collar 33 and the enlarged part 11 of the body 2. This enables the outlet fitting 4 to translate axially with respect to the body 2 between the retracted position represented in FIGS. 7 and 8 and the advanced position represented in FIG. 9. The tubular body of elastic material 15 tends normally to keep said fitting 4 in the retracted position illustrated in FIGS. 7 and 8: an elastic axial compression of the body 15 enables the outlet fitting 4 to translate from the retracted position to the advanced position of FIG. 9. On account of said elastic compression, the tubular body 15 conveniently (but not necessarily) has the conformation more clearly visible in FIG. 12. It presents a generally cylindrical end portion 38 in sliding-seal contact, via one or more integral rings 39, with an axial shank 40 of the outlet fitting 4, and an annular flange 41, on which said shank 40 rests at the front. The remaining part of the elastic tubular body 15, up to its end 17 resting against the collar 13 of the inner tubular element 6 of the inlet fitting 3, is formed with the helical grooves 20 and helical projections 21 already described previously.

Operation of the connector according to this embodiment is described in what follows.

Figure 7:
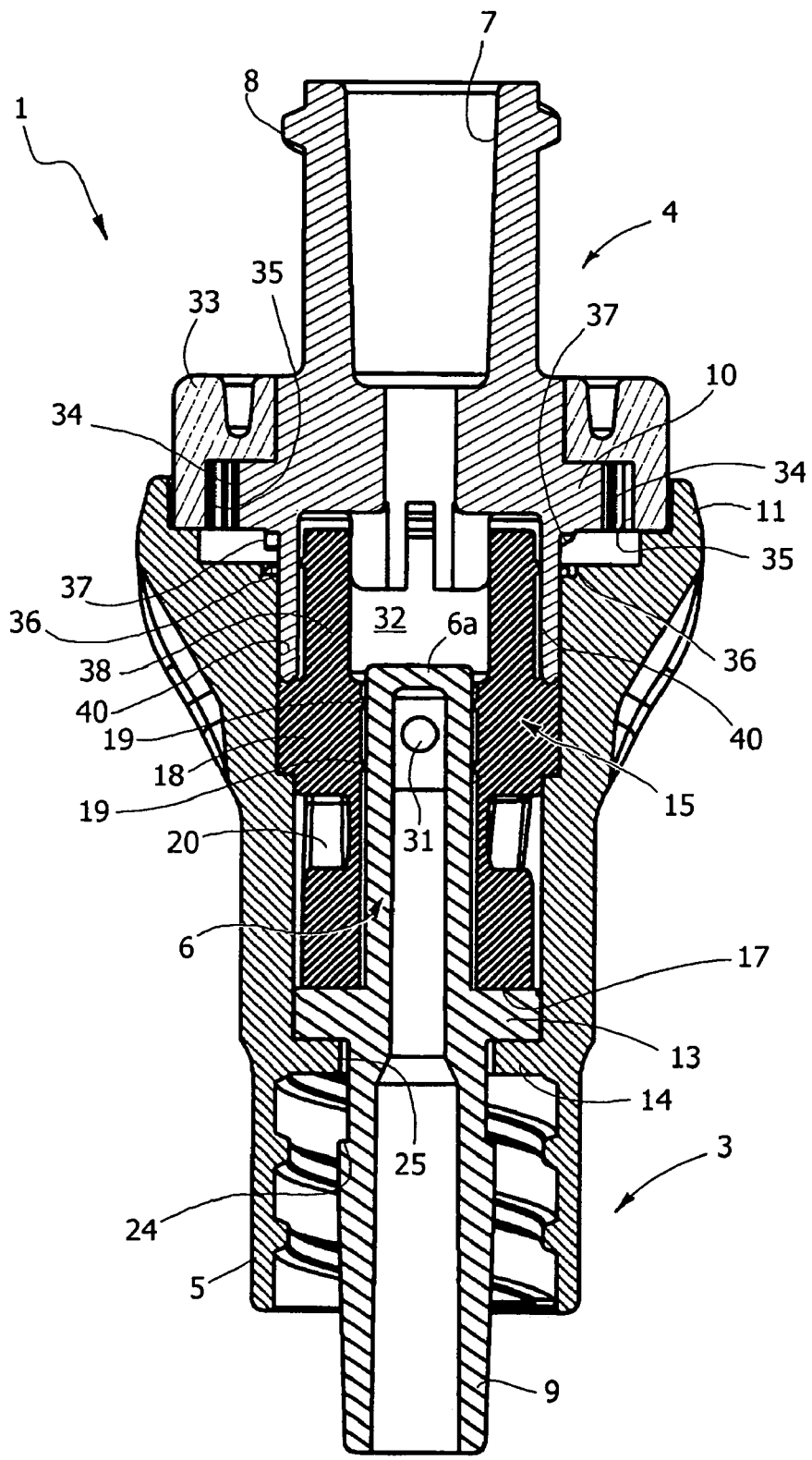
FIG. 7 is an axial cross-sectional view of the connector of FIG. 6 in a first operating condition.

When the outlet fitting 4 is in its normal retracted position shown in FIGS. 7 and 8, the complementary male luer-lock fitting can be easily screwed thereon thanks to the blocking in rotation, in the direction corresponding to that of screwing of said complementary male luer-lock fitting, performed by the first detent assembly 34-35. Once screwing is completed, unscrewing of the complementary male luer-lock fitting is not allowed as a result of the free rotation in said direction of the fitting 4 with respect to the body 2.

Figure 9:
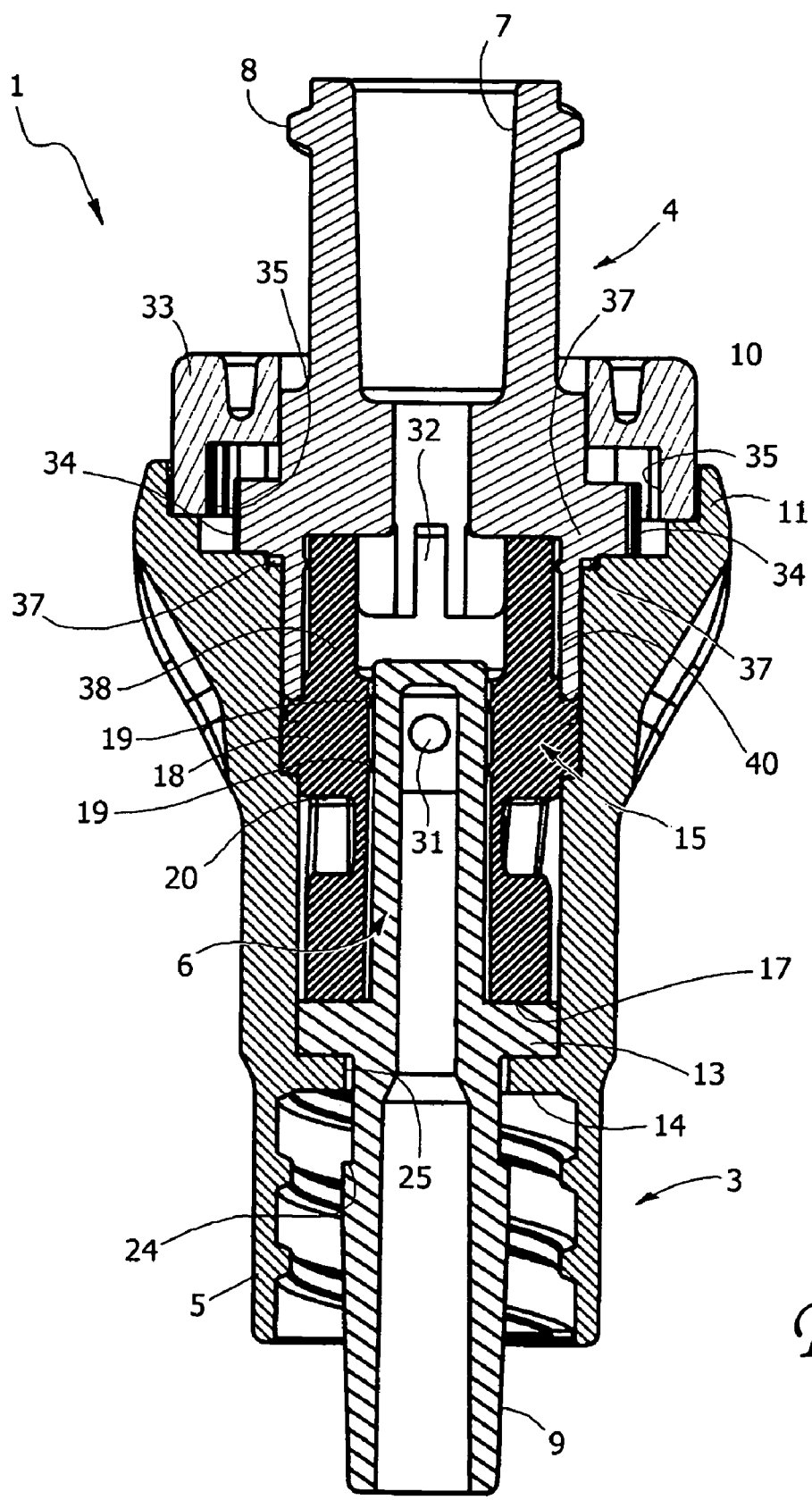
FIG. 9 is a view similar to that of FIG. 7 in a third operating condition.
Figure 10:
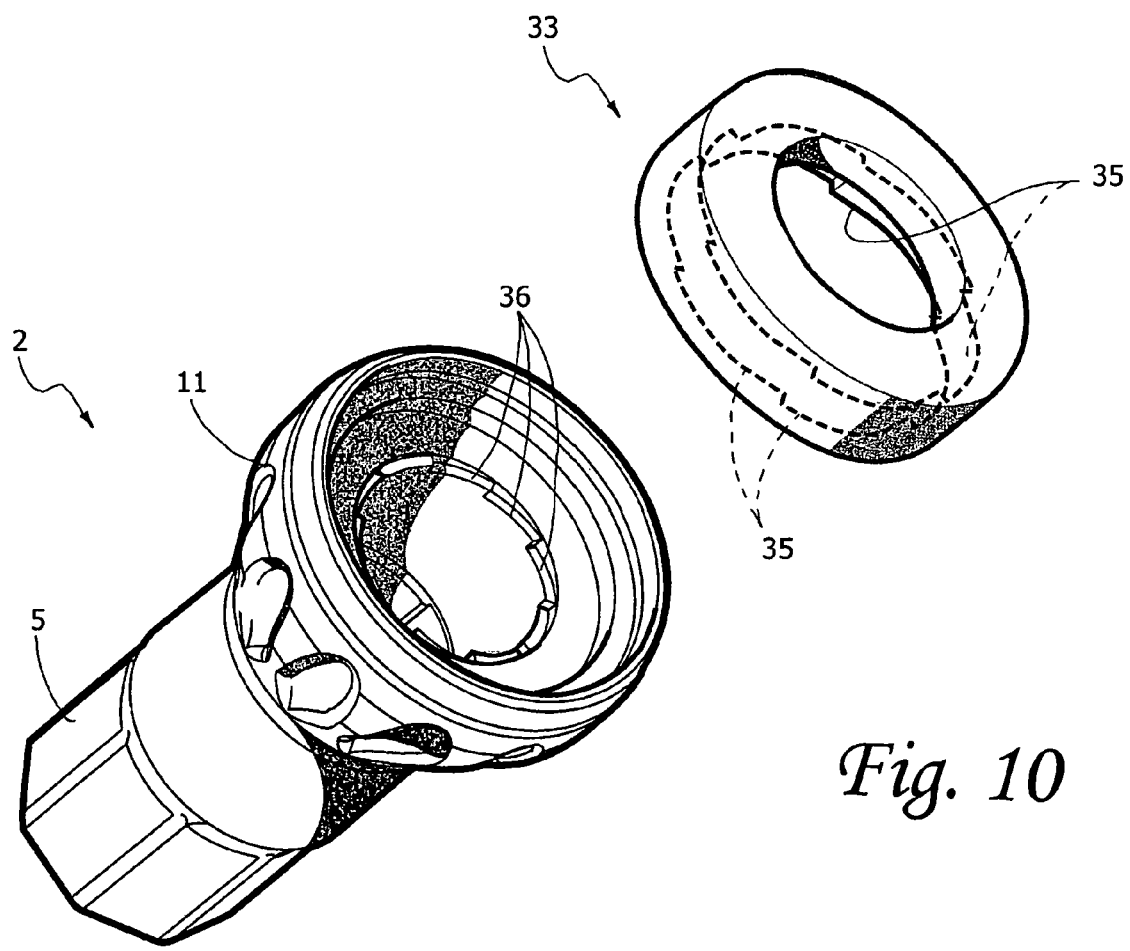
FIG. 10 is an exploded perspective view at a larger scale of the body of the connector represented in FIGS. 6 to 9.

In order to be able then to unscrew the complementary male luer-lock fitting from the outlet fitting 4, the fitting 4 must be translated positively in an axial direction from the retracted position of FIGS. 7 and 8 to the advanced position of FIG. 9. As a result of said translation, engagement of the second detent assembly 36-37 is obtained. In this way, the fitting 4 is blocked in rotation in the direction opposite to the previous one, i.e., in the direction corresponding to that of unscrewing of the complementary male luer-lock fitting, which can in this way be disengaged from the connector 1. It is therefore evident that the detachment between the connector 1 and a medical line connected to the complementary male luer-lock fitting requires a preliminary voluntary action of axial displacement of the fitting 4 from the retracted position to the advanced one. As soon as the action is removed, the elastic tubular body 15 brings the outlet fitting 4 back into the retracted position shown in FIGS. 7 and 8.

With the arrangement described above, it is moreover possible to provide a further safety function, as a result of which the displacement of the outlet fitting 4 from the retracted position to the advanced one, and hence the consequent possibility of removal of the complementary male luer-lock fitting screwed on said outlet fitting 4, is prevented as long as the inlet fitting 3 is in turn engaged with a corresponding complementary female luer-lock fitting. Said supplementary function is readily understandable from FIG. 8, which, as mentioned previously, corresponds to the advanced position of the inner tubular element 6 of the inlet fitting 3. In this position, the end 6a of the inner tubular element 6 is at the front adjacent to the internal part of the outlet fitting 4, the axial displacement of which from the retracted position to the advanced position is therefore prevented. As a result, unscrewing of a complementary male luer-lock fitting from the outlet fitting 4 is inhibited, on the basis of what has been described previously.

Only unscrewing of the complementary female luer-lock fitting from the inlet fitting 3 enables, as a result of the return of the inner tubular element 6 from the advanced position to the retracted position, axial translation of the outlet fitting 4 from the retracted position to the advanced one, thus enabling unscrewing of the complementary male luer-lock fitting from the outlet fitting 4.

It should be noted that the conformation of the teeth of the two detent assemblies 34-36 and 35-37 is purely indicative, given that the same functional effects could be obtained with equivalent systems such as front toothings, conical surfaces or other functionally equivalent solutions.

The variant represented in FIGS. 13 to 17 differs from the embodiment of FIGS. 6 to 12 basically as regards the presence of a system of manual engagement, via which the inner tubular element 6 of the inlet fitting 3 can be displaced axially from the retracted position to the advanced position even in the absence of a complementary female luer-lock connector coupled to said inlet fitting 3. This system of engagement envisages the presence of a pair of shaped manoeuvring tabs 42 carried, in the way more clearly visible in FIG. 17, by a pair of radial arms 43 formed integrally with a collar 44, which is in turn integral with the inner tubular element 6 of the inlet fitting 3. The arms 43 extend through respective axial slits 45 of the body 2, preventing rotation of the inner tubular element 6 with respect to the body 2, in such a way that the tabs 42 can be actuated from outside the connector 1 for axial translation of the inner tubular element 6 from the retracted position represented in FIG. 14, corresponding to closing of the passage of flow between the fittings 3 and 4, to the advanced position represented in FIG. 15, corresponding to opening of the passage of flow.

Figure 15:
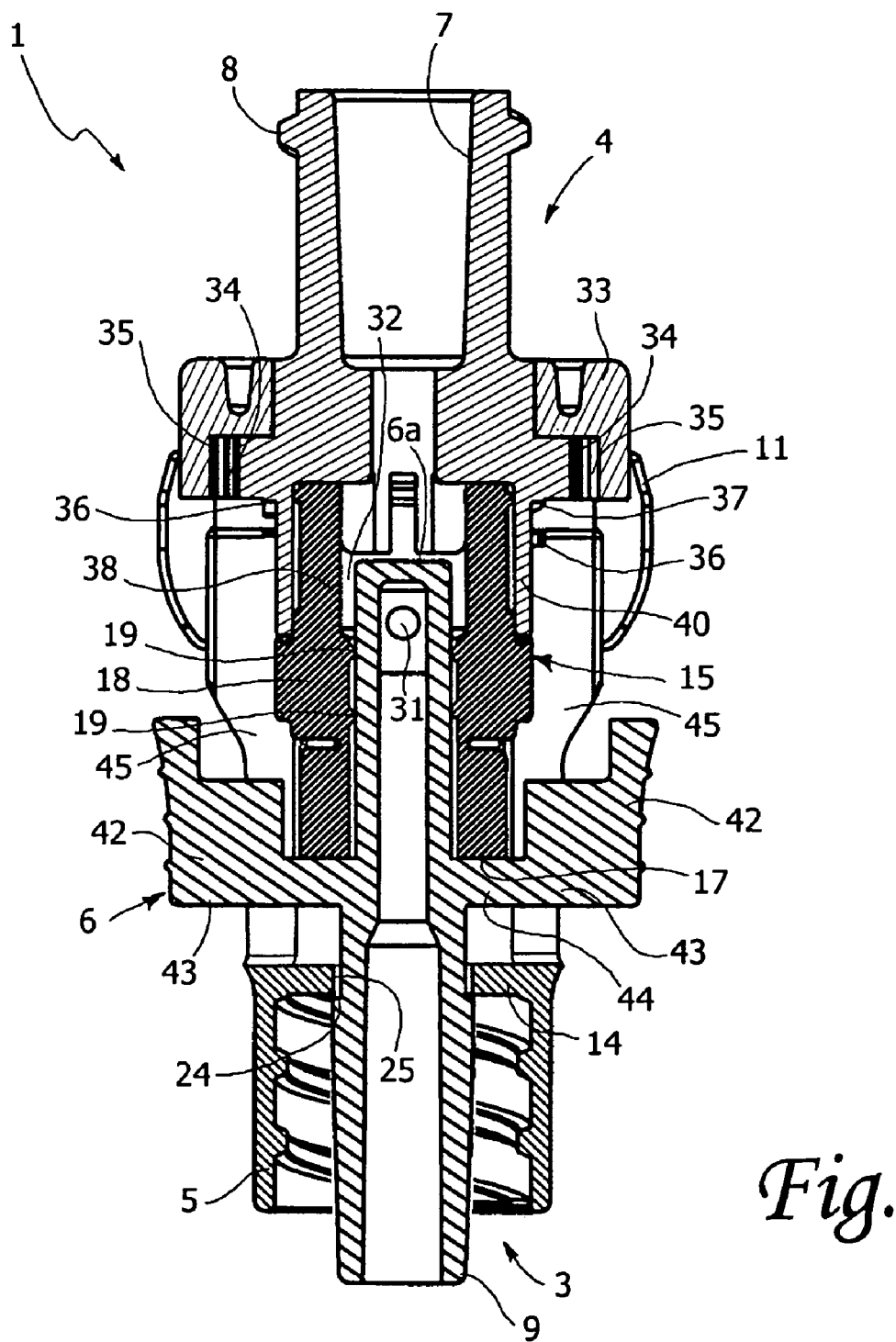
FIG. 15 is a view similar to that of FIG. 14 in a second operating condition.
Figure 16:
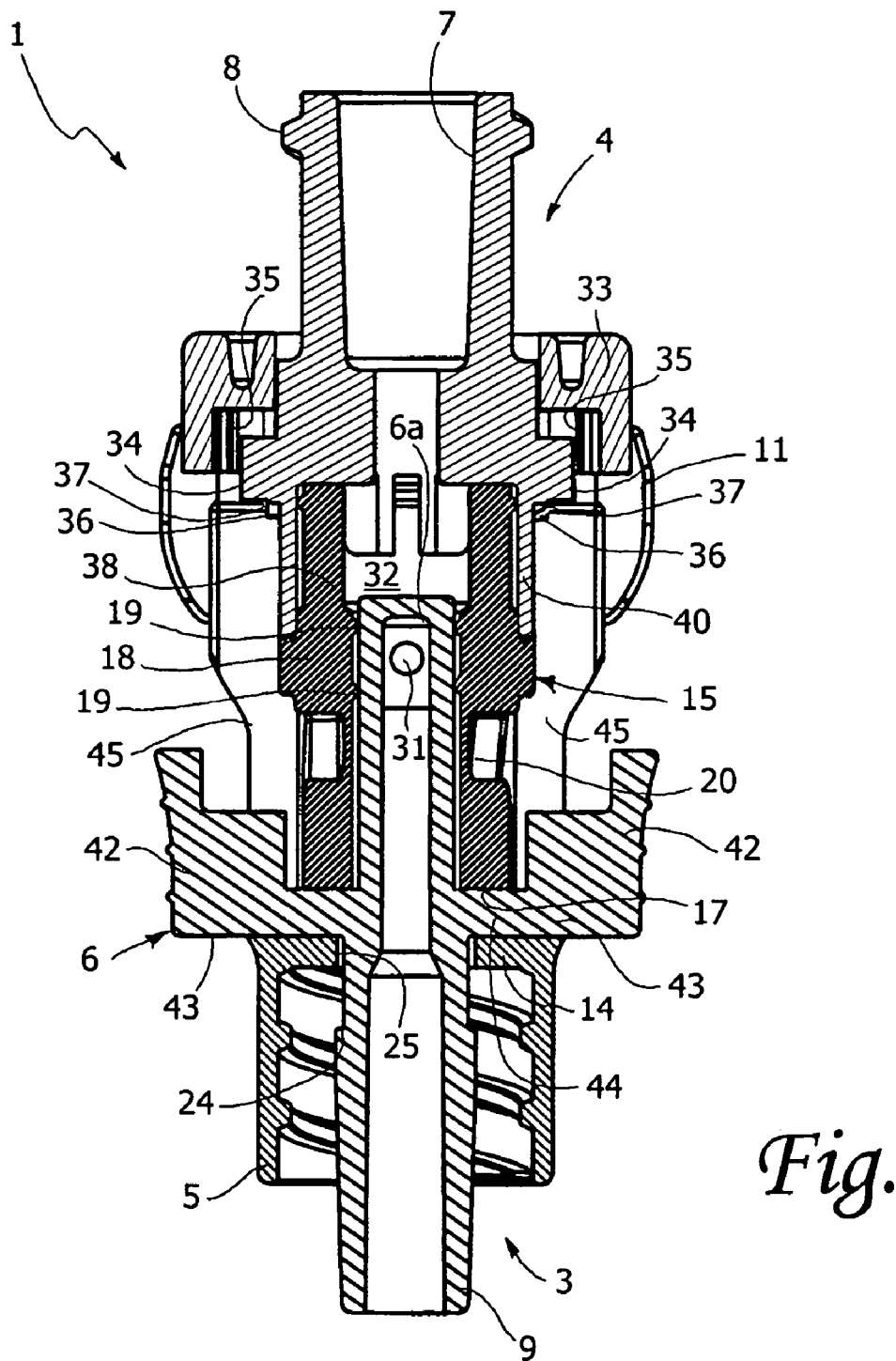
FIG. 16 is a view similar to those of FIGS. 14 and 15 in a third operating condition of the connector.
Figure 17:
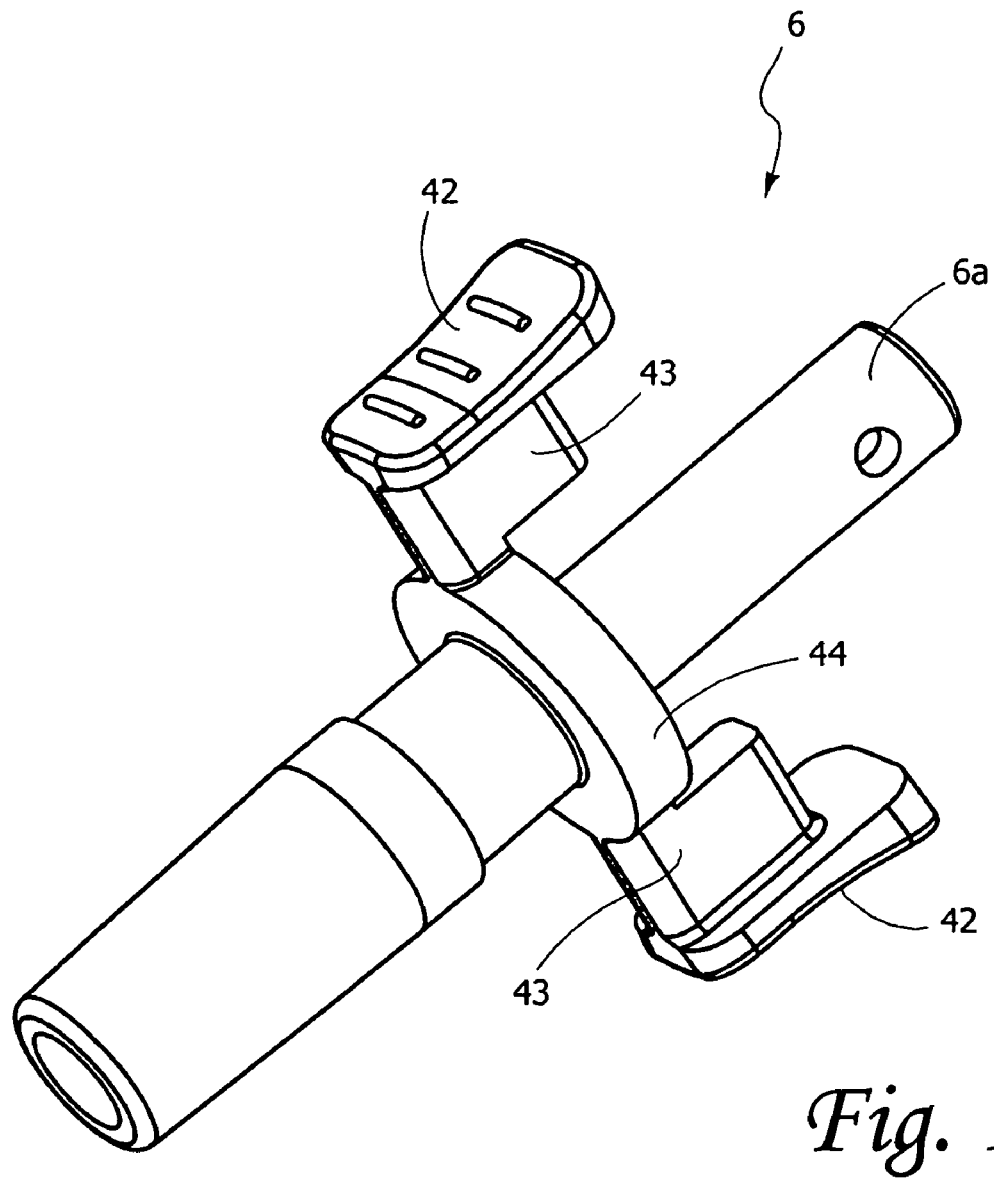
FIG. 17 is a perspective view at a larger scale of a detail of the connector represented in FIGS. 13 to 16.

In the position of FIG. 15, axial displacement of the outlet fitting 4 from the retracted position to the advanced one is likewise prevented. FIG. 16 illustrates, instead, the axially advanced position of the outlet fitting 4, in the retracted position of the outer tubular element 6, to enable unscrewing of the complementary male luer-lock fitting engaged with said outlet fitting 4 with the same modalities already described previously with reference to FIG. 9.

Figure 18:
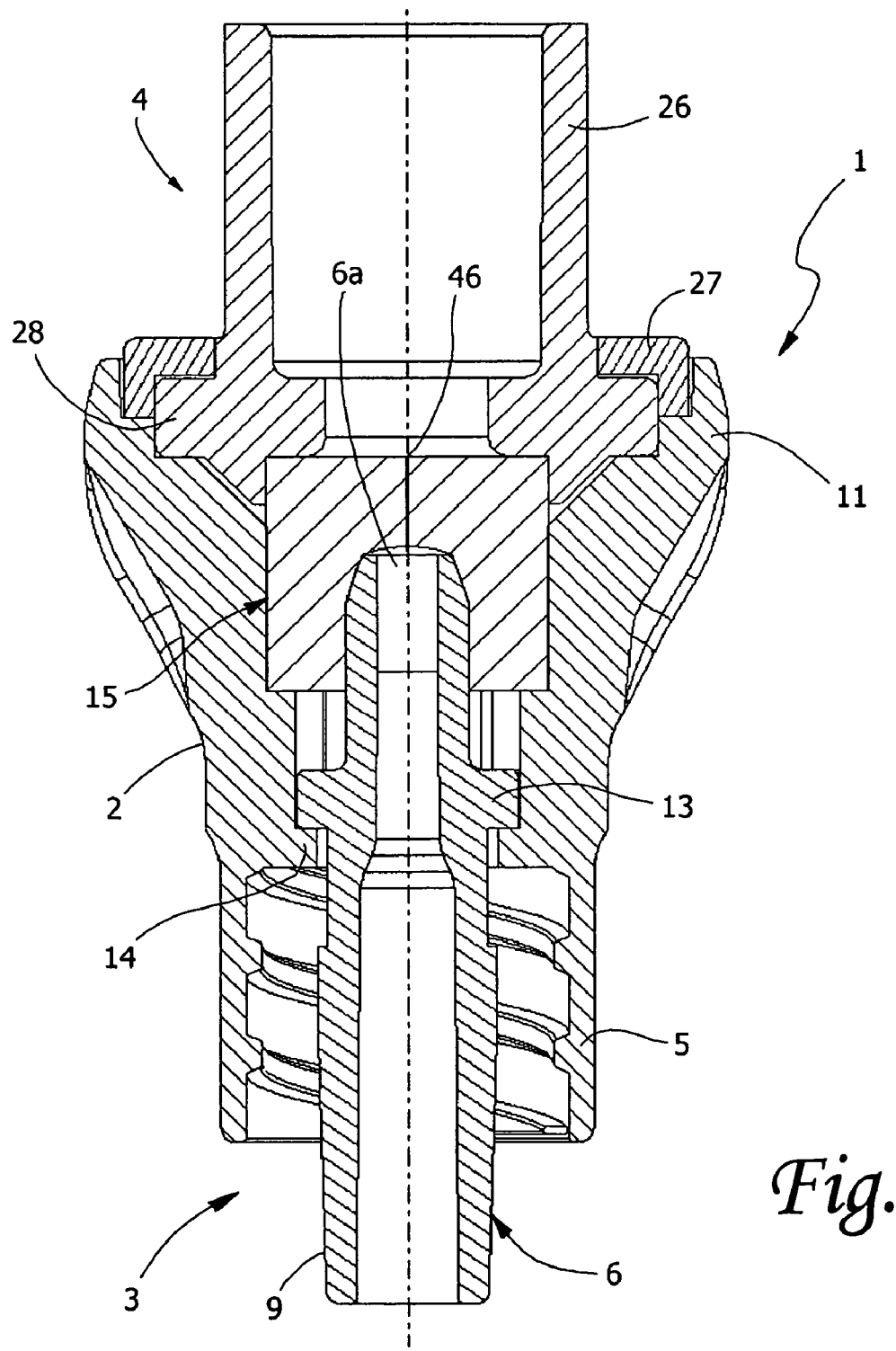
FIG. 18 is an axial sectional view of a fifth variant of the connector according to the invention, represented in a first operating condition.
Figure 19:
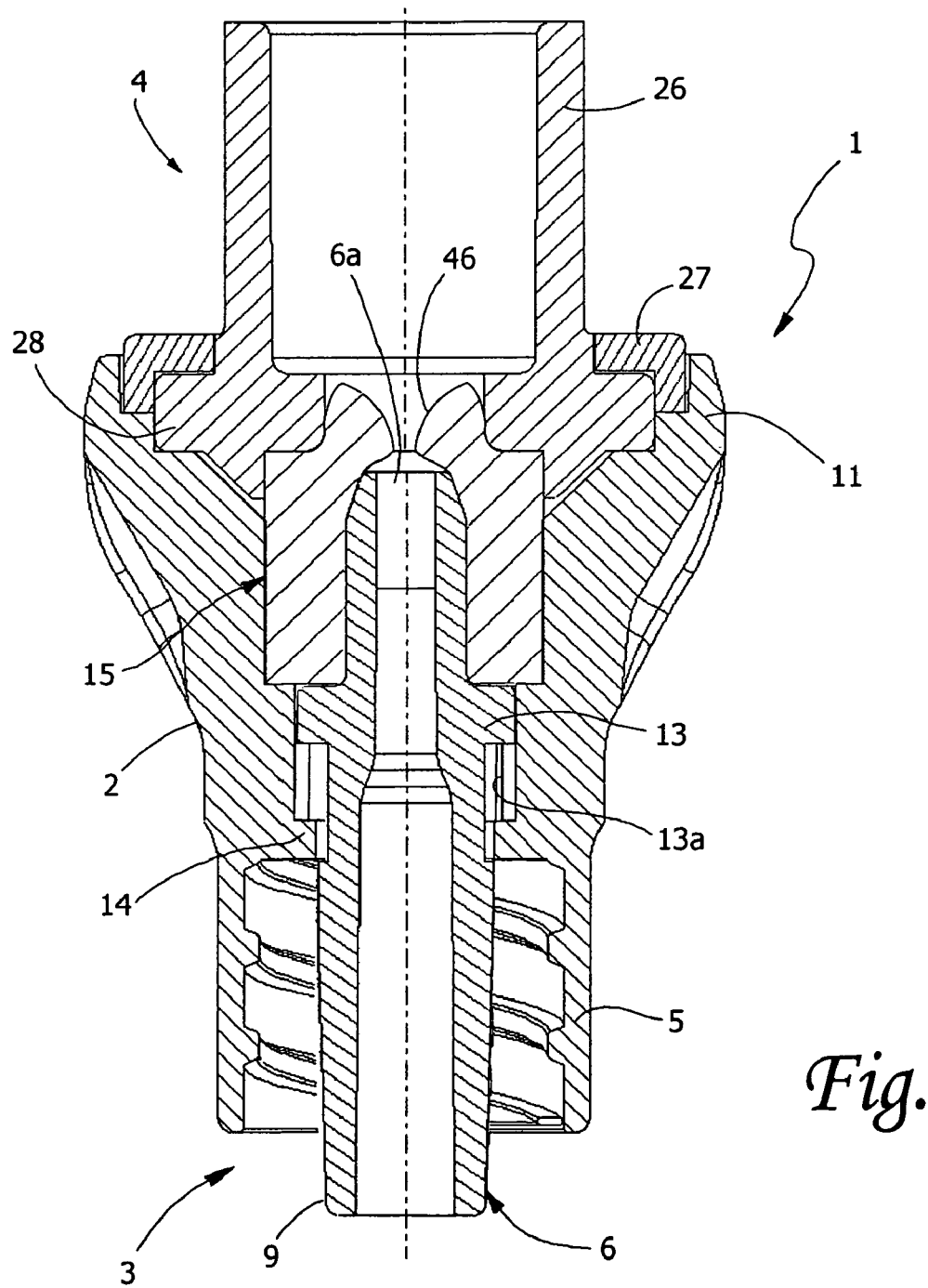
FIG. 19 is a view similar to that of FIG. 18 in a second operating condition of the connector.

The further variant of the connector represented in FIGS. 18 and 19 is particularly simple and compact from the constructional standpoint. In said variant, in which the outlet fitting 4 has, by way of example, a conformation similar to that of the fitting 26 of FIG. 5, the body of elastic material 15 that, according to the invention, performs the functions of sliding seal between the outer tubular element 6 and the body 2, of elastic thrust member to keep said inner tubular element 6 in the retracted position, and of delimitation of the passage of flow between the fittings 3 and 4 consists of a simple element of a generally cylindrical shape having an axial cut or through central slit 46, pressed in (as will be seen, partial) hermetic seal under the action of an appropriate radial preloading of assembly of the elastic body 15 within the body 2. In this case, the open end 6a of the inner tubular element 6 of the inlet fitting 3 is partially wedged and engaged within the elastic body 15 also in the retracted position of said inner tubular element 6, represented in FIG. 18, thus keeping the cut 46 partially open. Following upon engagement of a complementary female luer-lock fitting with the inlet fitting 3, the inner tubular element 6 translates axially towards the outlet fitting 4, as in the previous embodiments, thus completely opening the cut 46 so as to open the passage of flow between the fittings 3 and 4, in the way represented in FIG. 19. As may be seen in FIG. 19, the end 6a does not traverse the elastic body 15, but in any case keeps the cut 46 open thanks to its further wedging within said elastic body 15. In this condition, the body 15 sets itself consequently in a tubular condition, as in the embodiments described previously, keeping the passage of flow between the fittings 3 and 4 open.

When the complementary female luer-lock fitting is unscrewed from the inlet fitting 3, the elastic return of the body 15 towards the undeformed condition pushes the outer tubular element 6 back into the retracted position of FIG. 18, so as to provide the partial reclosing of the cut 46 in order to close the passage of flow between the fittings 3 and 4 hermetically.

It should be noted that, even though in the foregoing description and in the ensuing claims the fitting 3 is constantly referred to as inlet fitting and the fitting 4 is constantly referred to as outlet fitting, the flow through the connector 1 could be reversed, i.e., the fitting 4 can define the inlet fitting and the fitting 3 can define, in this case, the outlet fitting.

Of course, the details of construction and the embodiments may vary widely with respect to what is described and illustrated herein purely by way of example, without thereby departing from the scope of the present invention, as defined in the ensuing claims.

What is claimed is:

1. A medical valve connector comprising:
   a tubular body having an inlet fitting of the male luer or luer-lock type which can be coupled by screwing with a complementary female luer or luer-lock fitting;
   an outlet fitting coaxial to said inlet fitting, said outlet fitting at a distal end and said inlet fitting at a proximal end of said body; and
   means defining a passage of flow between said inlet and outlet fittings,
   said male inlet fitting comprising an outer internally-threaded tubular element and an inner tubular element, said inlet fitting bounded at a distal end by a collar separating said inlet fitting from an internal chamber, said collar having an opening allowing said inner tubular element to extend from said inlet fitting into said chamber;
   said inner tubular element having an outer end and an inner end and being axially open at both said inner and said outer ends, said inner tubular element being axially displaceable but not rotationally displaceable with respect to said outer tubular element and to said body, following coupling with said complementary female fitting, from a retracted closing position to an advanced position for opening said passage of flow;
   said inner tubular element comprising a flange in said internal chamber, said flange extending radially from said opening to an inner surface of said tubular body and abutting said collar in said retracted position, said inner tubular element having a diameter smaller than said flange distal of said flange and proximal of said flange;
   sliding-seal means between said inner tubular element and said body, and elastic means tending to keep said inner tubular element in said retracted position, wherein said means defining the passage of flow, said sliding-seal means and said elastic means are integrated in a generally tubular unitary body of elastic material set axially in a sealed way between said inlet and outlet fittings and formed with a transverse diaphragm having a pre-cut which is opened elastically by said internal end of said inner tubular element when said inner tubular element is in said advanced opening position.

2. The connector according to claim 1, wherein said inner tubular element of said male inlet fitting has a closed internal end and has in the proximity thereof at least one radial passage, and said body of elastic material defines a chamber open towards said outlet fitting and within which said at least one radial passage sets itself in said advanced opening position.

3. The connector according to claim 1, wherein said seal means comprise at least one integral internal annular projection of said body of elastic material.

4. The connector according to claim 1, further comprising means of axial arrest between said outer tubular element of said inlet fitting and said body in said retracted closing position.

5. The connector according to claim 1, further comprising means of axial arrest between said inner tubular element of said inlet fitting and said body in said advanced opening position.

6. The connector according to claim 1, wherein said outlet fitting consists of a female luer-lock fitting that can be engaged by screwing with a complementary male luer-lock fitting.

7. The connector according to claim 6, wherein said female luer-lock outlet fining is connected to said body in a rotary and axially translatable way from a retracted position to an advanced position against the action of said body of elastic material and wherein first and second one-directional detent means are provided, of which the first prevent rotation between said outlet fining and said body in a first direction of rotation corresponding to screwing of said complementary male luer-lock fining with said outlet fitting when the latter is set in said retracted position, and the second prevent rotation between said outlet fitting and said body in a second direction of rotation corresponding to unscrewing of said complementary male luer-lock fitting from said outlet fining when said outlet fining is translated into said advanced position.

8. The connector according to claim 7, wherein said first one-directional detent means include a ring of sprung pawls carried by said outlet fining in a first axial position, and a corresponding ring of saw teeth carried by said body in a first corresponding axial position.

9. The connector according to claim 8, wherein said second one-directional detent means include a ring of saw teeth carried by said outlet fitting in a second axial position staggered with respect to said first axial position, and a corresponding ring of detent teeth carried by said body in a second corresponding axial position.

10. The connector according to claim 7, wherein said inner tubular element of said inlet fitting prevents, in said advanced position, axial translation of said outlet fitting from said retracted position to said advanced position.

11. The connector according to claim 1, wherein said outlet fitting comprises a tubular element of direct connection to a pipe.

12. The connector according to claim 1, wherein said outlet fitting is connected to the body in a rotary way.

13. The connector according to claim 1, wherein said inner tubular element of said inlet fitting is provided with manoeuvring means projecting on the outside of said body for controlling manually axial displacement of said inner tubular element from said retracted position to said advanced position.

14. The connector according to claim 1, wherein said inner tubular element of said inlet fitting has an open internal end and said body of elastic material is formed with a central axial through slit; said internal end of said inner tubular element of said inlet fitting in said retracted position being wedged within said body of elastic material, keeping said central slit partially open, and in said advanced position still remaining partially engaged within said body of elastic material, opening said central slit completely.

15. The connector according to claim 1 wherein said inner tubular element comprises a projecting portion proximal of said flange, said projecting portion having a diameter larger than said opening, said projecting portion axially arresting said inner tubular element in said advanced opening position by contacting said collar and inhibiting distal movement of said inner tubular element.

16. The connector according to claim 1 wherein said flange abuts said sliding-seal means in said retracted position and said advanced position.

17. A medical valve connector comprising:
- a tubular body having an inlet fitting of the male luer or luer-lock type couplable by screwing with a complementary female luer or luer-lock fitting;
- an outlet fitting coaxial to said inlet fitting, said outlet fitting at a distal end and said inlet fitting at a proximal end of said body; and
- said male inlet fitting comprising an outer internally-threaded tubular element and an inner tubular element, said inlet fitting bounded at a distal end by a collar separating said inlet fitting from an internal chamber, said collar having an opening allowing said inner tubular element to extend from said inlet fitting into said chamber, said chamber allowing flow between said inlet and outlet fittings;
- said inner tubular element having a distal end and a proximal end and being axially open at both said distal end and said proximal end, said inner tubular element being axially displaceable but not rotationally displaceable with respect to said outer tubular element and to said body, following coupling with said complementary female fitting, from a retracted closing position to an advanced position for opening a passage of flow between said distal end and said proximal end of said inner tubular element;
- said inner tubular element comprising a flange in said internal chamber, said flange extending radially from said opening to an inner surface of said tubular body and abutting said collar in said retracted position, said inner tubular element having a diameter smaller than said flange distal of said flange and proximal of said flange;
- said inner tubular element comprising a projecting portion proximal of said flange, said projecting portion having a diameter larger than said opening, said projecting portion axially arresting said inner tubular element in said advanced opening position by contacting said collar and inhibiting distal movement of said inner tubular element;
- sliding-seal means between said inner tubular element and said body, and elastic means tending to keep said inner tubular element in said retracted position, wherein said sliding-seal means and said elastic means are integrated in a generally tubular unitary body of elastic material set axially in a sealed way between said inlet and outlet fittings and formed with a transverse diaphragm having a pre-cut which is opened elastically by said distal end of said inner tubular element when said inner tubular element is in said advanced opening position.

18. The connector according to claim 17 wherein said flange abuts said sliding-seal means in said retracted position and said advanced position.

* * * * *

UNITED STATES PATENT AND TRADEMARK OFFICE
CERTIFICATE OF CORRECTION

PATENT NO. : 7,666,170 B2 Page 1 of 1
APPLICATION NO. : 11/492747
DATED : February 23, 2010
INVENTOR(S) : Gianni Guala It is certified that error appears in the above-identified patent and that said Letters Patent is hereby corrected as shown below:

Title Page, Item (73) Assignee: Delete "Moncaleri" and insert --Moncalieri--

Claim 7, at Column 10, lines 19, 24, 26, 30 and 31: Delete "fining" and insert --fitting--

Claim 8, at Column 10, line 34: Delete "fining" and insert --fitting--

Signed and Sealed this

Eighteenth Day of May, 2010

David J. Kappos
*Director of the United States Patent and Trademark Office*